United States Patent [19]
Casey

[11] Patent Number: 5,975,470
[45] Date of Patent: Nov. 2, 1999

[54] MEDICINE VIAL HOLDING DEVICE

[76] Inventor: John Casey, 8546 Spohn Dr., Fontana, Calif. 92335

[21] Appl. No.: 09/015,204

[22] Filed: Jan. 29, 1998

[51] Int. Cl.[6] .................................................. A47G 23/02
[52] U.S. Cl. ......................... 248/146; 248/121; 248/165; 248/176.1
[58] Field of Search ............................ 248/105, 99, 159, 248/176.1, 311.3, 313, 316.1, 316.7, 346.03, 346.04, 346.3, 346.5, 146, 152, 154, 121, 165

[56] References Cited

U.S. PATENT DOCUMENTS

| | | | |
|---|---|---|---|
| D. 364,943 | 12/1995 | Valentine et al. ..................... | 248/121 X |
| 3,167,291 | 1/1965 | Maguire ............................. | 278/346.3 X |
| 3,298,648 | 1/1967 | Sepanski ............................. | 248/105 X |
| 3,361,265 | 1/1968 | Wernimont ........................ | 248/176.1 X |
| 3,368,783 | 2/1968 | Deutsch ............................ | 248/176.1 X |
| 4,461,387 | 7/1984 | Belokin, Jr. ......................... | 248/159 X |
| 4,848,714 | 7/1989 | Ziaylek, Jr. et al. .................... | 248/313 |
| 5,386,958 | 2/1995 | Amato ..................................... | 248/146 |
| 5,924,659 | 7/1999 | Babcock ................................. | 248/146 |

*Primary Examiner*—Derek J. Berger

[57] ABSTRACT

A new medicine vial holding device for holding a medicine vial so that a user may extract medicine from the vial with a syringe. The inventive device includes a base and a support member which is upwardly extended from the upper surface of the base member. The back portion of a clip member is coupled to the first surface of the support member so that the clip member is positioned towards the top side of the support member. The clip member also has a pair of spaced apart arms adapted to hold a medicine vial therebetween.

19 Claims, 2 Drawing Sheets

MEDICINE VIAL HOLDING DEVICE

BACKGROUND OF THE INVENTION

1. Field of the Invention

The present invention relates to medicine vial holders and more particularly pertains to a new medicine vial holding device for holding a medicine vial so that a user may extract medicine from the vial with a syringe.

2. Description of the Related Art

The use of medicine vial holders is known in the prior art. More specifically, medicine vial holders heretofore devised and utilized are known to consist basically of familiar, expected and obvious structural configurations, notwithstanding the myriad of designs encompassed by the crowded prior art which have been developed for the fulfillment of countless objectives and requirements.

Known prior art medicine vial holders include U.S. Pat. No. 3,982,716; U.S. Pat. No. 5,056,744; U.S. Pat. No. 4,278,225; U.S. Pat. No. 4,971,209; U.S. Pat. No. 3,938,769; U.S. Pat. No. Des. 328,216.

While these devices fulfill their respective, particular objectives and requirements, the aforementioned patents do not disclose a new medicine vial holding device. The inventive device includes a base and a support member which is upwardly extended from the upper surface of the base member. The back portion of a clip member is coupled to the first surface of the support member so that the clip member is positioned towards the top side of the support member. The clip member also has a pair of spaced apart arms adapted to hold a medicine vial therebetween.

In these respects, the medicine vial holding device according to the present invention substantially departs from the conventional concepts and designs of the prior art, and in so doing provides an apparatus primarily developed for the purpose of holding a medicine vial so that a user may extract medicine from the vial with a syringe.

SUMMARY OF THE INVENTION

In view of the foregoing disadvantages inherent in the known types of medicine vial holders now present in the prior art, the present invention provides a new medicine vial holding device construction wherein the same can be utilized for holding a medicine vial so that a user may extract medicine from the vial with a syringe.

The general purpose of the present invention, which will be described subsequently in greater detail, is to provide a new medicine vial holding device apparatus and method which has many of the advantages of the medicine vial holders mentioned heretofore and many novel features that result in a new medicine vial holding device which is not anticipated, rendered obvious, suggested, or even implied by any of the prior art medicine vial holders, either alone or in any combination thereof.

To attain this, the present invention generally comprises a base and a support member which is upwardly extended from the upper surface of the base member. The back portion of a clip member is coupled to the first surface of the support member so that the clip member is positioned towards the top side of the support member. The clip member also has a pair of spaced apart arms adapted to hold a medicine vial therebetween.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new medicine vial holding device apparatus and method which has many of the advantages of the medicine vial holders mentioned heretofore and many novel features that result in a new medicine vial holding device which is not anticipated, rendered obvious, suggested, or even implied by any of the prior art medicine vial holders, either alone or in any combination thereof.

It is another object of the present invention to provide a new medicine vial holding device which may be easily and efficiently manufactured and marketed.

It is a further object of the present invention to provide a new medicine vial holding device which is of a durable and reliable construction.

An even further object of the present invention is to provide a new medicine vial holding device which is susceptible of a low cost of manufacture with regard to both materials and labor, and which accordingly is then susceptible of low prices of sale to the consuming public, thereby making such medicine vial holding device economically available to the buying public.

Still yet another object of the present invention is to provide a new medicine vial holding device which provides in the apparatuses and methods of the prior art some of the advantages thereof, while simultaneously overcoming some of the disadvantages normally associated therewith.

Still another object of the present invention is to provide a new medicine vial holding device for holding a medicine vial so that a user may extract medicine from the vial with a syringe.

Yet another object of the present invention is to provide a new medicine vial holding device which includes a base and a support member which is upwardly extended from the upper surface of the base member. The back portion of a clip member is coupled to the first surface of the support member so that the clip member is positioned towards the top side of the support member. The clip member also has a pair of spaced apart arms adapted to hold a medicine vial therebetween.

Still yet another object of the present invention is to provide a new medicine vial holding device that is able to be used to fill a syringe with medicine from a medicine vial containing a hypodermically injected medicine while only using one hand thereby making it easy for people with limited limb function to easily administer medicine to themselves.

Even still another object of the present invention is to provide a new medicine vial holding device that is easily collapsible for convenient storage.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
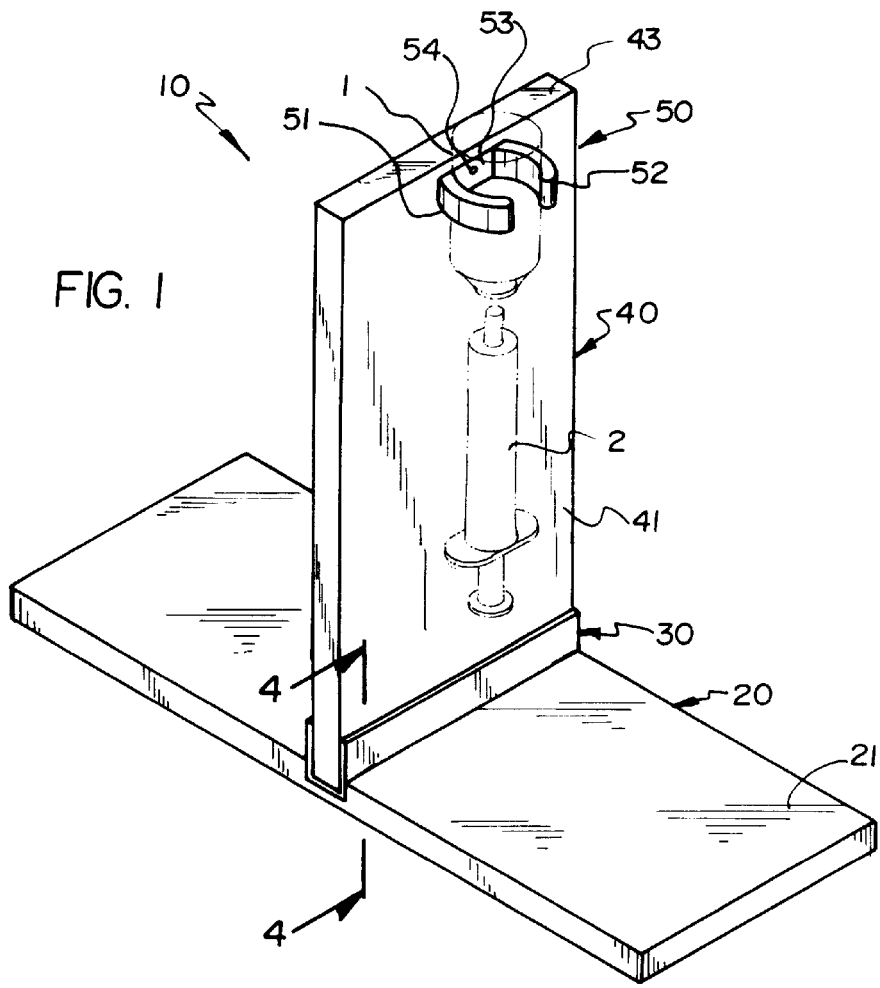
FIG. 1 is a schematic perspective view of a new medicine vial holding device in use according to the present invention.
Figure 2:
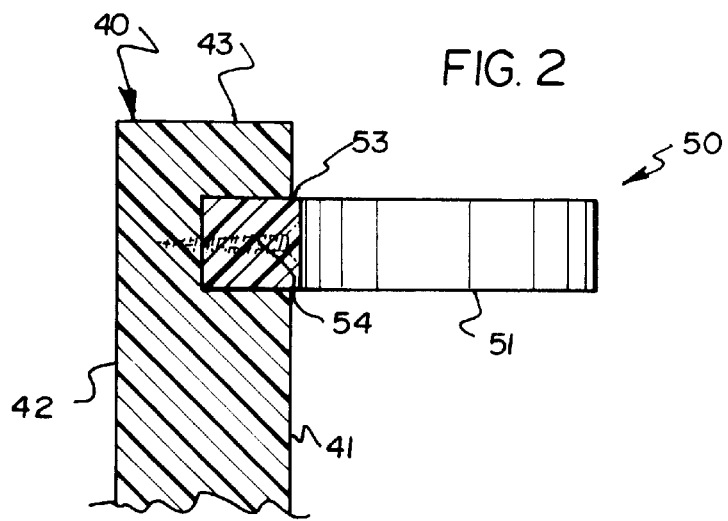
FIG. 2 is a schematic partial cross sectional view of the clip member of the present invention.
Figure 3:
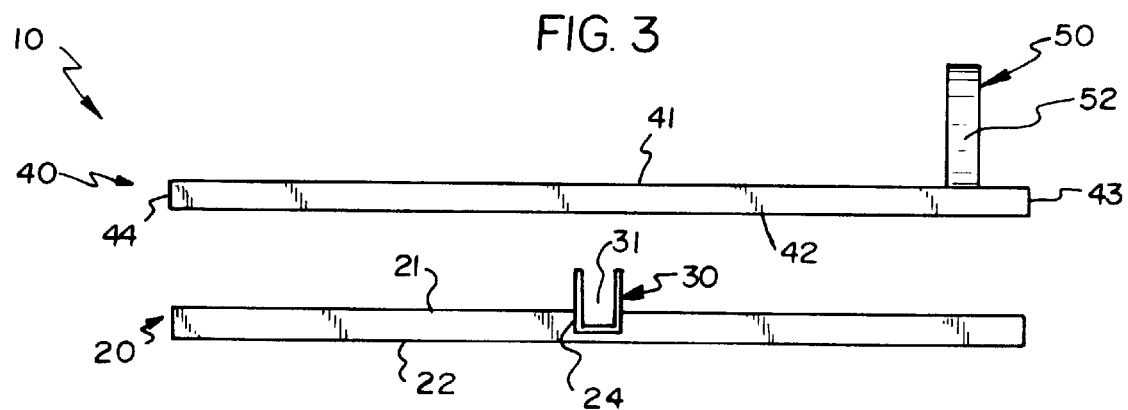
FIG. 3 is a schematic side view of the present invention in the a disassembled state.

With reference now to the drawings, and in particular to FIGS. 1 through 4 thereof, a new medicine vial holding device embodying the principles and concepts of the present invention and generally designated by the reference numeral 10 will be described.

As best illustrated in FIGS. 1 through 4, the medicine vial holding device 10 generally comprises a base 20 and a support member 40 which is upwardly extended from the upper surface 21 of the base 20 member. The back portion of a clip member 50 is coupled to the first surface of the support member 40 so that the clip member 50 is positioned towards the top side of the support member 40. The clip member 50 also has a pair of spaced apart arms 51,52 adapted to hold a medicine vial therebetween.

As illustrated in FIG. 1, the medicine vial holding device 10 is designed for holding a vial 1 containing a hypodermically injected medicine therein so that the medicine can be removed by a syringe 2 (and easily with one hand).

The base 20 is generally rectangular and has upper and lower surfaces 21,22, a pair of short sides and a pair long sides. The upper and lower surfaces 21,22 of the base 20 defining a base thickness therebetween. Preferably, the base thickness is less than about 1 inch. Even more preferably, the base thickness is less than about ½ inch. Ideally, the base 20 thickness is about ⅜ inch. The long sides of the base 20 define a base width therebetween. Preferably, the base width is less than about 6 inches. Ideally, the base 20 width is about 5½ inches. The short sides of the base 20 define a base length therebetween. Preferably, the base length is less than about 12 inches. Ideally, the base length is about 10 inches.

Figure 4:
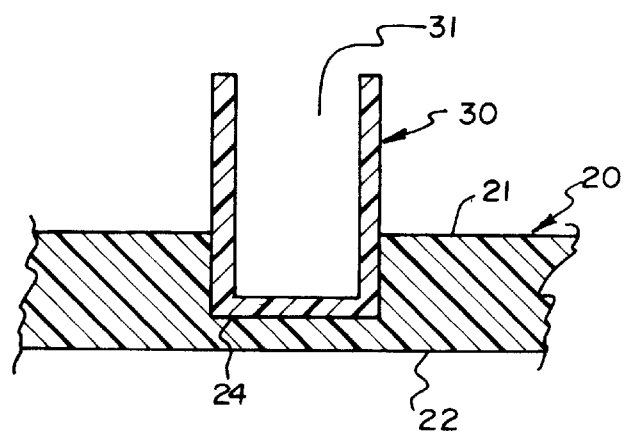
FIG. 4 is a schematic cross sectional view of the present invention taken from line 4—4 from FIG. 1.

As best illustrated in FIGS. 1 and 4, the upper surface 21 of the base 20 has an elongate base channel 24. The base channel 24 has a length and preferably a generally rectangular U-shaped cross section taken substantially perpendicular to its length. The length of the base channel 24 is extended between the long sides of the base 20 and is preferably generally parallel with the short sides of the base 20.

In the preferred embodiment of the invention, an elongate mounting bracket 30 is inserted into the base channel 24. The mounting bracket 30 has an upper bracket channel 31 which is extended along the length of the mounting bracket 30. The mounting bracket 30 is inserted into the base channel 24 such that the upper bracket channel 31 faces upwards. The mounting bracket 30 preferably has a generally rectangular U-shaped cross section taken substantially perpendicular to it length of the mounting bracket 30 so that it may fit in the base channel 24. Ideally, the length of the mounting bracket 30 is about the base length. Thus, ideally the length of the mounting bracket 30 should be less than about 6 inches and preferably 5½ inches.

The support member 40 is preferably generally rectangular and has first and second surfaces 41,42, top and bottom sides 43,44, and a pair of lateral sides. The bottom side 44 of the support member 40 is removably inserted into the upper bracket channel 31 of the mounting bracket 30 such that the support member 40 is upwardly extended from the upper surface of the base 20 member. Preferably, the support member 40 is extended generally perpendicular to the base 20 member. The first and second surfaces 41,42 of the support member 40 define a support member 40 thickness therebetween. Preferably, the support member 40 thickness is less than about 1 inch. Even more preferably, the support member 40 thickness is less than about ½ inch. Ideally, the support member 40 thickness is about ⅜ inch. The lateral sides of the support member 40 define a support member 40 width therebetween. Preferably, the support member 40 width is less than about 6 inches. Ideally, the support member 40 width is about 5½ inch. The top and bottom sides 43,44 of the support member 40 define a support member 40 length therebetween. Preferably, the support member 40 length is generally equal to the base 20 length.

The clip member 50 is generally C-shaped and has a pair of spaced apart arms 51,52 and a back portion 53. The arms 51,52 of the clip member 50 are arcuate and adapted to hold a medicine vial 1 therebetween. The back portion 53 of the clip member 50 is coupled to the first surface of the support member 40. Preferably, a threaded fastener 54 couples the back portion 53 of the clip member 50 to the first surface of the support member 40. The clip member 50 is preferably positioned towards the top side of the support member 40.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A medicine vial holding device, comprising:
    a base having upper and lower surfaces, a pair of short sides and a pair of long sides;
    wherein said upper and lower surfaces of said base define a base thickness therebetween;
    wherein said long sides of said base define a base width therebetween;
    wherein said short sides of said base define a base length therebetween;
    a support member having first and second surfaces, top and bottom sides, and a pair of lateral sides,
    wherein said first and second surfaces of said support member define a support member thickness therebetween;
    wherein said lateral sides of said support member define a support member width therebetween;
    wherein said top and bottom sides of said support member define a support member length therebetween;
    said support member being upwardly extended from said upper surface of said base member; and
    a clip member being generally C-shaped and having a pair of spaced apart arms and a back portion, said arms of said clip member being arcuate and adapted to hold a medicine vial therebetween, said back portion of said clip member being coupled to said first surface of said support member, said clip member being positioned towards said top side of said support member for providing space between said clip member and said base for a syringe in an inverted position below a vial being held in said clip member;
    wherein said upper surface of said base has an elongate base channel;
    an elongate mounting bracket comprising an upper bracket channel with spaced walls, said mounting bracket being inserted into said base channel such that the spaced walls of said upper bracket channel extend upwards, said bottom side of said support member being inserted into said upper bracket channel of said mounting bracket such that the spaced walls of said upper bracket channel embrace the bottom side of said support member for providing a rigid mounting between said support member and said base member, said support member being removably inserted into said mounting bracket such that said support member may be removed from said base member for collapsing said support member and said base member into a form more easily transported by a user.

2. The device of claim 1, wherein said base and said support member are generally rectangular.

3. The device of claim 1, wherein said base thickness is less than about 1 inch, and wherein said support member thickness is less than about 1 inch.

4. The device of claim 3, wherein said base thickness is less than about ½ inch, and wherein said support member thickness is less than about ½ inch.

5. The device of claim 4, wherein said base thickness is less than about ⅜ inch, and wherein said support member thickness is less than about ⅜ inch.

6. The device of claim 1, wherein said base width is less than about 6 inches, and wherein said support member width is less than about 6 inches.

7. The device of claim 6, wherein said base width is less than about 5½ inches, and wherein said support member width is less than about 5½ inches.

8. The device of claim 1, wherein said base length is less than about 12 inches, and wherein said support member length is less than about 12 inches.

9. The device of claim 8, wherein said base length is less than about 10 inches, and wherein said support member length is less than about 10 inches.

10. The device of claim 1, wherein said support member length is generally equal to said base length.

11. The device of claim 1, wherein said elongate base channel has a length, said length of said base channel being extended between said long sides of said base, said length of said base channel being generally parallel with said short sides of said base.

12. The device of claim 11, wherein said elongate base channel has a generally rectangular U-shaped cross section taken substantially perpendicular to said length of said base channel, and wherein said mounting bracket has a generally rectangular U-shaped cross section taken substantially perpendicular to said length of said mounting bracket.

13. The device of claim 11, wherein said length of said mounting bracket is about equal to said base width.

14. The device of claim 1, wherein said support member is extended generally perpendicular to said base member.

15. The device of claim 1, wherein a threaded fastener couples said back portion of said clip member to said first surface of said support member.

16. The medicine vial holding device of claim 1 wherein a bottom of the upper bracket channel is recessed below the upper surface of the base member.

17. A medicine vial holding device, comprising:
    a base being generally rectangular and having upper and lower surfaces, a pair of short sides and a pair of long sides;
    wherein said upper and lower surfaces of said base define a base thickness therebetween, wherein said base thickness is about ⅜ inch;
    wherein said long sides of said base define a base width therebetween, wherein said base width is about 5½ inches;
    wherein said short sides of said base define a base length therebetween, wherein said base length is about 10 inches;
    said upper surface of said base having an elongate base channel having a length and a generally rectangular U-shaped cross section taken substantially perpendicular to said length of said base channel, said length of said base channel being extended between said long sides of said base, said length of said base channel being generally parallel with said short sides of said base;
    an elongate mounting bracket having a length and an upper bracket channel, said upper bracket channel being extended along said length of said mounting bracket, said mounting bracket having a generally rectangular U-shaped cross section taken substantially perpendicular to said length of said mounting bracket, wherein said length of said mounting bracket is about equal to said base width;

said mounting bracket being inserted into said base channel such that said upper bracket channel faces upwards;

a support member being generally rectangular and having first and second surfaces, top and bottom sides, and a pair of lateral sides, wherein said first and second surfaces of said support member defining a support member thickness therebetween, wherein said support member thickness is about ⅜ inch;

wherein said lateral sides of said support member define a support member width therebetween, wherein said support member width is about 5½ inches;

wherein said top and bottom sides of said support member define a support member length therebetween, wherein said support member length is generally equal to said base length;

said bottom side of said support member being removably inserted into said upper bracket channel of said mounting bracket such that said support member is upwardly extended from said upper surface of said base member, wherein said support member is extended generally perpendicular to said base member; and a clip member being generally C-shaped and having a pair of spaced apart arms and a back portion, said arms of said clip member being arcuate and adapted to hold a medicine vial therebetween, said back portion of said clip member being coupled to said first surface of said support member, wherein a threaded fastener couples said back portion of said clip member to said first surface of said support member, said clip member being positioned towards said top side of said support member for providing space between said clip member and said base for a syringe in an inverted position below a vial being held in said clip member;

wherein spaced walls of said upper bracket channel extend upwards, said bottom side of said support member being inserted into said upper bracket channel of said mounting bracket such that the spaced walls of said upper bracket channel embrace the bottom side of said support member for providing a rigid mounting between said support member and said base member, said support member being removably inserted into said mounting bracket such that said support member may be removed from said base member for collapsing said support member and said base member into a form more easily transported by a user.

18. A portable collapsible medicine vial holding system, comprising:

a base having upper and lower surfaces, a pair of short sides and a pair of long sides;

wherein said upper and lower surfaces of said base define a base thickness therebetween;

wherein said long sides of said base define a base width therebetween;

wherein said short sides of said base define a base length therebetween;

a support member having first and second surfaces, top and bottom sides, and a pair of lateral sides, wherein said first and second surfaces of said support member define a support member thickness therebetween;

wherein said lateral sides of said support member define a support member width therebetween;

wherein said top and bottom sides of said support member define a support member length therebetween;

said support member being upwardly extended from said upper surface of said base member;

a clip member being generally C-shaped and having a pair of spaced apart arms and a back portion, said arms of said clip member being arcuate and adapted to hold a medicine vial therebetween, said back portion of said clip member being coupled to said first surface of said support member, said clip member being positioned towards said top side of said support member; and a medicine vial inserted between the arms of the clip member such that the medicine vial is held by the clip member, said medicine vial being in an inverted position with a top of the medicine vial opening downwardly.

19. The medicine vial holding system of claim 18 additionally comprising a syringe having a needle and a barrel with graduations marked on said barrel, said syringe being inverted with the needle extending into the top of the medicine vial for facilitating reading of the graduations on said barrel.

* * * * *